(12) United States Patent
Hadváry et al.

(10) Patent No.: US 11,166,660 B2
(45) Date of Patent: Nov. 9, 2021

(54) DERMALLY AFFIXED DEVICE FOR INTRAVENOUS ACCESS

(75) Inventors: Paul Hadváry, Biel-Benken (CH); Hansjörg Tschirky, Sissach (CH)

(73) Assignee: PHARMASENS AG, Biel-Benken (CH)

(*) Notice: Subject to any disclaimer, the term of this patent is extended or adjusted under 35 U.S.C. 154(b) by 475 days.

(21) Appl. No.: 14/009,614

(22) PCT Filed: Mar. 28, 2012

(86) PCT No.: PCT/EP2012/055463
§ 371 (c)(1),
(2), (4) Date: Dec. 5, 2013

(87) PCT Pub. No.: WO2012/136528
PCT Pub. Date: Oct. 11, 2012

(65) Prior Publication Data
US 2014/0114211 A1      Apr. 24, 2014

(30) Foreign Application Priority Data

Apr. 5, 2011  (EP) ..................................... 11161179
Apr. 21, 2011 (EP) ..................................... 11163344

(51) Int. Cl.
*A61B 5/15*       (2006.01)
*A61M 39/02*      (2006.01)
*A61M 5/142*      (2006.01)

(52) U.S. Cl.
CPC ... *A61B 5/150992* (2013.01); *A61M 5/14248* (2013.01); *A61M 39/0247* (2013.01);
(Continued)

(58) Field of Classification Search
CPC ........ A61B 5/150992; A61M 39/0247; A61M 5/14248; A61M 2039/0258;
(Continued)

(56) References Cited

U.S. PATENT DOCUMENTS 3,500,828 A * 3/1970 Podhora ............ A61M 25/0693
                                                     604/168.01
3,757,771 A * 9/1973 Ruegg ................. A61M 25/0111
                                                          600/360
(Continued)

FOREIGN PATENT DOCUMENTS

WO    WO2006/067217 A2    6/2006
WO    WO2008/080990 A1    7/2008

OTHER PUBLICATIONS

Espacenet, bibliographic data of priority application PCT/EP2012/055463.*

*Primary Examiner* — David J. McCrosky
(74) *Attorney, Agent, or Firm* — Xsensus LLP

(57) ABSTRACT

An improved, injection or blood removal device for intravenous access has a port with a septum at the exterior end of an intravenous catheter, a coupling element having an adhesive surface for securing attachment onto the skin, an injection or blood sampling unit, a connecting cannula piercing the septum of the port, and means to secure functional assembly. Attachment of the device to the skin covering or close to the intravenous puncture site and without long communicating tubes allows ambulant injection of drugs or measuring of concentration-time profiles of exogenous and endogenous analytes to improve treatment modalities on an individualized basis.

17 Claims, 5 Drawing Sheets

(52) U.S. Cl.
CPC ............... *A61M 2039/027* (2013.01); *A61M 2039/0258* (2013.01); *A61M 2039/0282* (2013.01)

(58) Field of Classification Search
CPC .... A61M 2039/027; A61M 2039/0282; A61M 2005/14264; A61M 2005/14268; A61M 39/02; A61M 5/1413
See application file for complete search history.

(56) References Cited

U.S. PATENT DOCUMENTS

| | | | | |
|---|---|---|---|---|
| 3,906,930 A * | 9/1975 | Guerra | ............... | A61B 5/15003 600/579 |
| 3,996,923 A * | 12/1976 | Guerra | ............... | A61B 5/15003 600/579 |
| 4,106,491 A * | 8/1978 | Guerra | ............... | A61B 5/15003 251/149.2 |
| 4,150,089 A * | 4/1979 | Linet | ................. | A61B 5/15003 215/6 |
| 4,250,880 A * | 2/1981 | Gordon | ................ | A61M 25/02 128/DIG. 26 |
| 4,469,151 A * | 9/1984 | Wilson | ................. | B01L 3/0217 118/408 |
| 4,474,538 A * | 10/1984 | Schmid-Schonbein | ...................... | A61M 1/1089 128/DIG. 12 |
| 4,585,435 A * | 4/1986 | Vaillancourt | ....... | A61M 5/1408 604/126 |
| 4,673,394 A | 6/1987 | Fenton, Jr. et al. | | |
| 4,753,651 A | 6/1988 | Eckenhoff | | |
| 5,165,406 A * | 11/1992 | Wong | ................. | A61B 5/15003 204/409 |
| 5,423,334 A * | 6/1995 | Jordan | ................ | A61B 5/0031 128/899 |
| 5,523,092 A * | 6/1996 | Hanson | ..................... | A61F 2/06 424/423 |
| 5,755,709 A * | 5/1998 | Cuppy | .............. | A61M 25/0606 604/164.12 |
| 5,858,005 A | 1/1999 | Kriesel | | |
| 5,928,194 A * | 7/1999 | Maget | ............... | A61M 5/14248 604/131 |
| 6,190,352 B1 * | 2/2001 | Haarala | ............. | A61M 39/0208 604/288.02 |
| 6,391,018 B1 * | 5/2002 | Tanaka | .............. | A61M 25/0041 604/164.13 |
| 6,582,403 B1 * | 6/2003 | Bierman | ................. | A61M 25/02 604/174 |
| 8,224,410 B2 * | 7/2012 | Hadvary | ............ | A61B 5/14514 600/310 |
| 2006/0253076 A1 * | 11/2006 | Butts | ................. | A61M 39/0247 604/167.06 |
| 2010/0256466 A1 * | 10/2010 | Shekalim | ........... | A61B 5/14525 600/317 |
| 2010/0298777 A1 * | 11/2010 | Nishtala | ........ | A61M 2039/0205 604/174 |
| 2012/0203177 A1 * | 8/2012 | Lanier, Jr. | ......... | A61M 5/14224 604/151 |
| 2012/0277667 A1 * | 11/2012 | Yodat | ................... | A61B 5/1451 604/65 |
| 2014/0031793 A1 * | 1/2014 | Constantineau | .. | A61M 5/14248 604/510 |
| 2015/0352277 A1 * | 12/2015 | De Polo | ............. | A61M 5/1413 604/151 |

* cited by examiner

Detail A

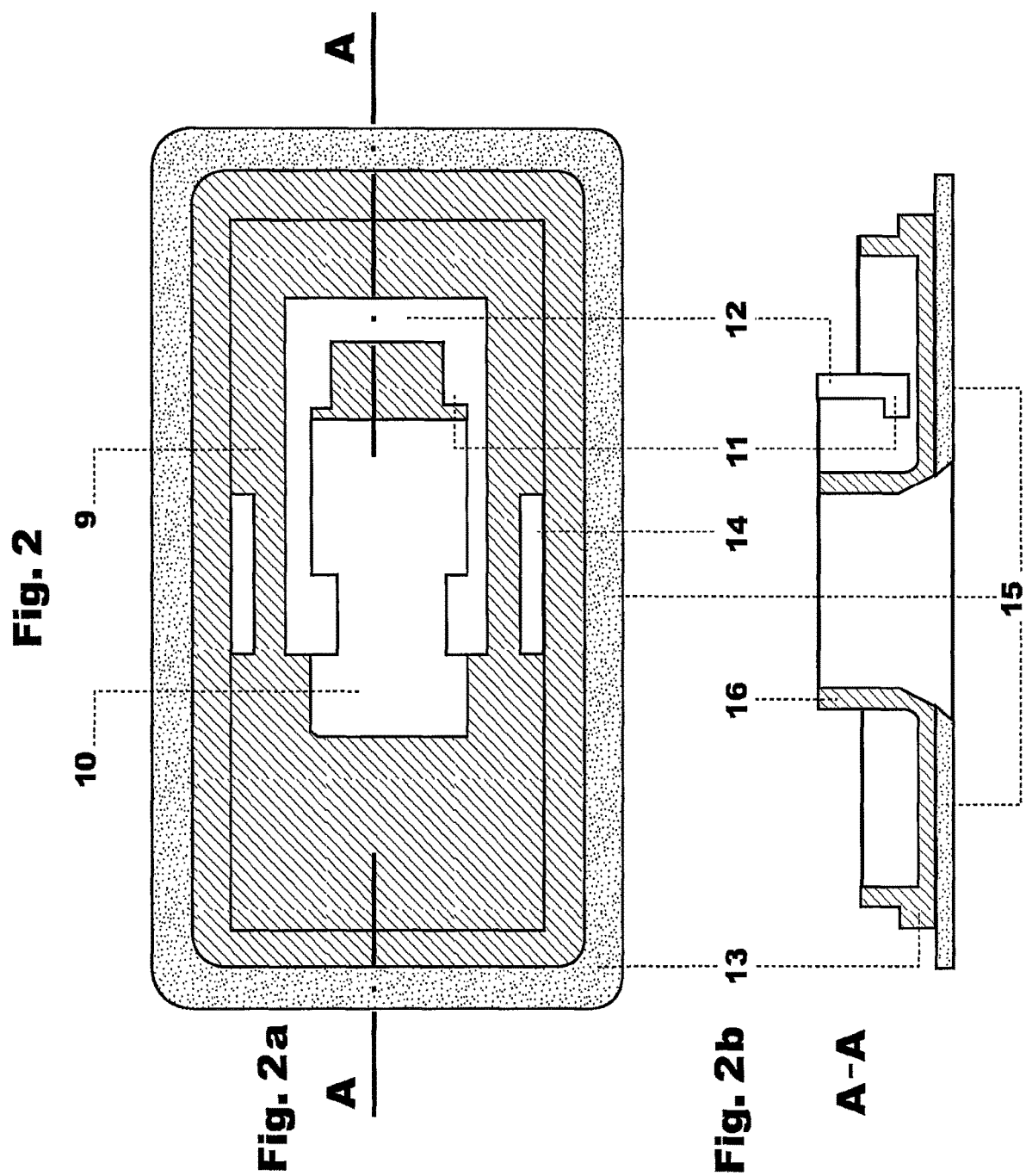

DERMALLY AFFIXED DEVICE FOR INTRAVENOUS ACCESS

CROSS-REFERENCE TO RELATED APPLICATIONS

This application is national stage application of International Application No. PCT/EP2012/055463, filed Mar. 28, 2012, which designates the U.S., and claims the benefit of priority from European Patent Application No. 11161179.4, filed Apr. 5, 2011, and from European Patent Application No. 11163344.2, filed Apr. 21, 2011. The entire contents of each of the above applications are hereby incorporated by reference herein in entirety.

Field of the Invention

The invention relates generally to intravenous injection and diagnostic devices, and specifically to devices having both a contact surface for attaching to a patient's skin and an intravenous cannula for introducing an injection fluid or removing blood.

Background of the Invention

Intravenous infusion devices are widely used in patient care but their size and complexity largely restricts their use to specialized facilities and almost precludes ambulatory use. Recently, ambulatory use of subcutaneous infusion devices has been pioneered in diabetes care for the delivery of insulin but similar devices are lacking for intravenous infusion covering the requirements for safe and convenient ambulatory use without impairing normal daily activities of the patient. Main drawbacks for ambulatory use are that they operate with connective tubes to an intravenous catheter and that they are too large and heavy for direct wearing by the patient and are therefore either stationary or attached to a stand.

For individualized health care monitoring of the level of endogenous analytes and drugs over a period of several hours to a few days would be important. This necessitates frequent blood sampling and can therefore normally only be done at specialized facilities or hospitals. The patient has normally to stay at the facility for the whole duration of the procedure, causing inconvenience and high costs. This precludes widespread use of such information in individualized medicine.

SUMMARY OF THE INVENTION

The aim of the present invention is to overcome the problems with the ambulant use of current intravenous injection systems or with serial blood sampling for analyte determination by incorporating tailored and improved individual components of the device and the co-operation of these components achieves a desired compactness resulting in small size and weight, thus allowing safe attachment to the skin.

More specifically, the aim of the present invention is a solution for intravenous delivery of injection fluid into a patient, or for removal of blood from a patient with a device which does not need long connecting tubes to the intravenous catheter and which can be worn by the patient directly adhering to the skin at the site of the intravenous access, allowing ambulatory use without disturbing normal daily activities.

According to the invention, the above problems are solved by an intravenous access device for intravenous delivery of injection fluid into a patient, or for removal of blood from a patient which is adhering to the skin and comprising: a port at the exterior end of an intravenous catheter having a cavity with at least one septums, an injection or blood sampling unit, and a coupling element having means for positioning and fixing the port and the injection or blood sampling unit relative to each other and having an adhesive contact surface for securing onto the patient.

The subject intravenous access device for introducing an injection fluid into a patient or removing blood through an intravenous catheter comprises a port with a septum at the exterior end of an intravenous catheter, a coupling element with an adhesive surface for securing attachment onto the skin and having means for positioning and fixing the port and the injection or blood sampling unit relative to each other and thereby piercing the septum of the port by a connecting cannula which secures free passage of injection fluid or blood between the injection or blood sampling unit and the intravenous catheter. Port, coupling element, and injection or blood sampling unit have means for simple, firm and functionally safe assembly. The connecting cannula has a tip which is configured for piercing the septum of the port and dimensioned for introducing an injection fluid into the patient or removing blood. Typically, piercing of the septum of the port with the connecting cannula is enforced by constructive elements and starting the infusion and/or blood sampling process is actuated automatically upon assembly.

In preferred embodiments, the inventive device has a connecting cannula which is fixedly positioned relative to the casing and pump of the injection or blood sampling unit. This allows a much simpler construction and higher reliability for performance than flexible connections.

The subject invention extends the advantages of patch pumps adhering directly to the skin for subcutaneous injection of drugs to an intravenous access within a single device without disturbing connecting tubes. The subject invention allows also easy ambulant sampling of blood e.g. for pharmacokinetics or the determination of circadian rhythms, but can also be used in hospital settings to determine analyte concentrations like glucose continuously with minimal blood withdrawal, being of high importance in the treatment of children or in the ICU. In preferred embodiments the injection or blood sampling unit has a syringe pump, preferably with a barrel curved in the shape of a segment of a toroidal tube resulting in a substantially reduced footprint and a desired reduction in overall size. In an alternative preferred embodiment, the inventive injection device has a flexible reservoir integrally combined with the connecting cannula for containing the injection fluid, manufactured preferably by blow-fill-seal technology and the delivery of injection fluid is effected by controlled compressing of the flexible reservoir.

In this specification the following definitions are used:

"Adhesive contact surface" for temporary wearing on the skin is made of materials with strong adhesive properties, stretchability and minimal allergenicity. This adhesive layer is fixed on the base of the device and preferentially the surface of the adhesive layer which is fixed to the skin is significantly larger than its surface which is fixed to the base of the device. This can be accomplished e.g. by an adhesive layer extending beyond the surface of the base of the device or, preferentially by using a shape for the adhesive surface to the skin similar to or only slightly larger than the surface of the base of the device but fixing it to the latter in such a way that an outer annular zone is not fixed to the base of the device. Such a design is described in EP0825882.

"Analyte" means any endogenous or exogenous substance the concentration of which can be used to diagnose the health, organ function, metabolic status, or drug metabolizing capacity of an individual. Examples of endogenous substances are glucose, lactate, oxygen, creatinine, etc. Examples of exogenous substances are drugs, metabolites of such drugs, diagnostic substances (e.g. inulin) etc.

"Blood sampling unit" is the functional element for collecting samples of blood for determination of analytes on-line within the device or externally to the device by, but not limited to biochemical, immunological, HPLC, or LC/MS/MS methods. Typically, it contains a pump allowing suction of fluid, e.g. a syringe pump, which is connected to the connecting cannula. For external analysis the samples can be collected in separated receptacles or in a continuous cavity, e.g. a tube taking precautions that mixing of samples taken at different times is reduced to a minimum. This can be achieved e.g. by introduction of segments of air or of a non-miscible fluid into the blood withdrawn creating separated samples in the continuous cavity.

"Connecting cannula" is a hollow needle with an outer diameter below 1 mm which is connected to the injection or the blood sampling unit and has a tip configured and dimensioned to allow easy penetration of the septum of the port. Insertion into the septum of the port can be achieved by pressing the injection or the blood sampling unit against the port, guided and reinforced by the coupling element.

"Coupling element" is a transition piece between the port and the injection or blood sampling unit. It has a flat or slightly concave base for attachment on the skin, e.g. of the forearm, and has means for its positioning above the port and for fixing the port, e.g. by a bolt mechanism. By means of an adhesive contact surface on its base the coupling element is attached and secured to the patient's skin holding also the port firmly attached. The coupling element has also means for positioning the injection or blood sampling unit relative to the port in such a way that the connecting cannula gets aligned with the septum of the port and by pressing the injection or the blood sampling unit against the coupling element holding the port the connecting cannula penetrates the septum of the port and thereby fluidly connects the injection or blood sampling unit with the intravenous catheter. Preferentially, the mechanism for fixing the injection or blood sampling unit to the coupling element is configured such that coupling is effected and re-enforced automatically upon pressing against each other, and de-coupling for disassembly is effected manually.

"Delivery of injection fluid" encompasses both relatively fast injection (bolus) and relatively slow introduction (also called infusion or instillation) of a liquid into the body.

"Drive and control means" contains all necessary mechanical, electronics and software elements for all necessary functions of the device like, but not limited to, delivery of injection fluid into a patient, or for removal of blood from a patient according to internal or external signals, initiating, controlling and surveying the correct functioning of the device, feeding and controlling the measuring means for analytes and transforming sensor signals into analyte measurements, storing, displaying and transmitting analyte measurements online or batch-wise, interacting with external devices, preferentially wirelessly, and giving warning signals if the device is not functioning properly or if analyte measurements are not within a pre-defined range.

"Injection unit" is the functional element for delivery of injection fluid and typically contains a reservoir, a pump, drive and control means and a connecting cannula. In some type of pumps such as syringe pumps or pressurized systems the reservoir is integral part of the pump mechanism, whereas in other types, like peristaltic or reciprocating piston pumps it's a separate entity. The reservoir can be pre-filled with the injection fluid or be filled just before use. Preferentially pump types allowing a compact construction and a form which can be conveniently worn attached to the patient's skin such as a syringe pump the barrel of which is curved in the shape of a segment of a toroidal tube or a pump with a flexible reservoir and compressed gas which is a drive from a gas generating cell, causing a positive displacement of injection fluid by compressing the collapsible reservoir.

"Intravenous catheter" is a small flexible tube consisting of synthetic polymers which is placed usually into a peripheral vein preferentially on the arm in order to administer medication or to draw blood. The catheter is introduced into the vein by a guide needle or guide wire (mandrin), which is subsequently removed while the catheter remains in place. The end of the catheter outside the vein ends in a cavity of the port and the port forms an integral part of the system for intravenous placing the catheter and removal of the guide needle or guide wire.

"Measuring means for analytes" is the functional element for the determination of analyte concentrations and means, but is not restricted to, any on-line analysis system, such as electrochemical, optic, thermometric, piezoelectric or magnetic measuring systems.

"Port" at the exterior end of an intravenous catheter comprises a casing with a cavity and one or more septums for coupling the intravenous catheter to the injection or blood sampling unit via a connecting cannula. Preferably, the port has a septum for retraction of the guide needle or guide wire after introduction of the intravenous catheter into the vein which is closing after removal.

"Septum" is a stopper made of natural or synthetic rubbertype material which can be pierced with a cannula or wire 20 in a contamination-free and tight way and upon removal of the cannula or wire closes itself off and becomes tight again. According to an embodiment, the port has a cavity with three or more integrated septums.

The term "intravenous access" is used for the connection between an inserted intravenous catheter and an external unit for either injecting a fluid through the catheter into the vein or removing blood therefrom.

An exemplified embodiment of the invention will now be described with reference to the accompanying drawings in which

DESCRIPTION OF THE DRAWINGS

FIG. 2 is a diagrammatic top and sectional view of a coupling element linking the injection or blood sampling unit to the port.

DESCRIPTION OF THE INVENTION

Figure 1A:
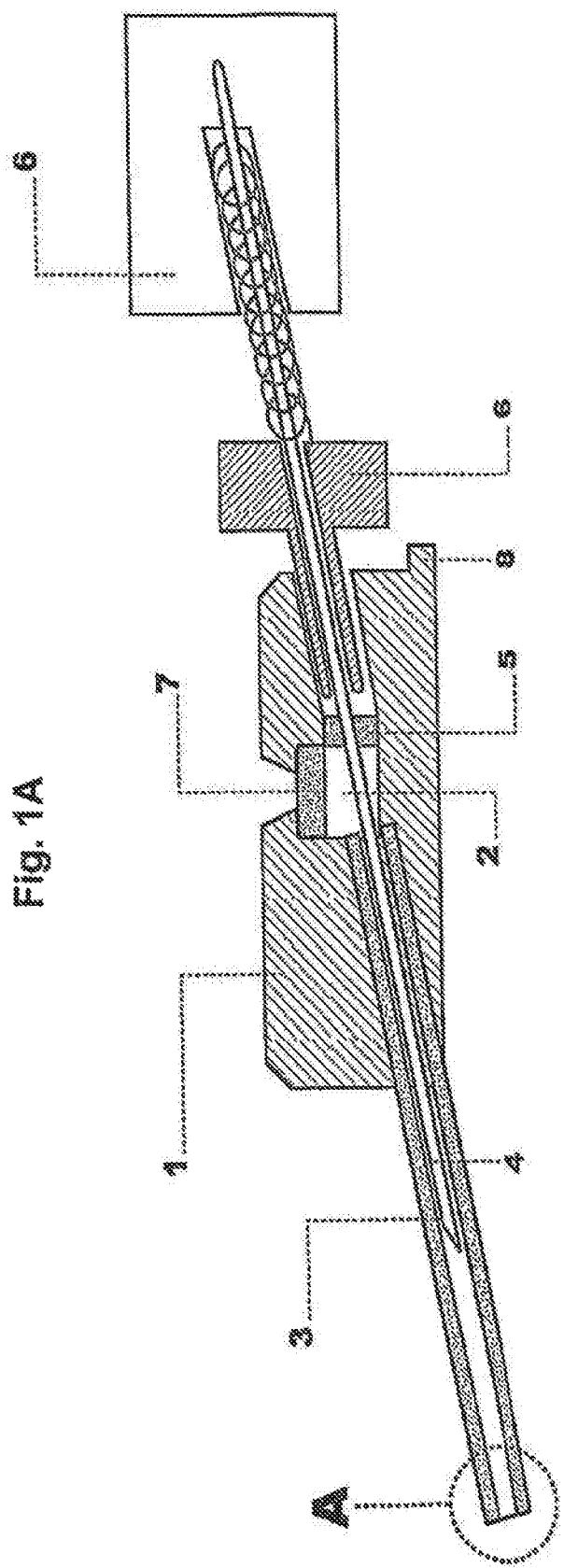
FIG. 1A is a diagrammatic sectional view of an intravenous access port at the exterior end of an intravenous catheter of a device for intravenous delivery of injection fluid into a patient, or for removal of blood from a patient.
Figure 1B:
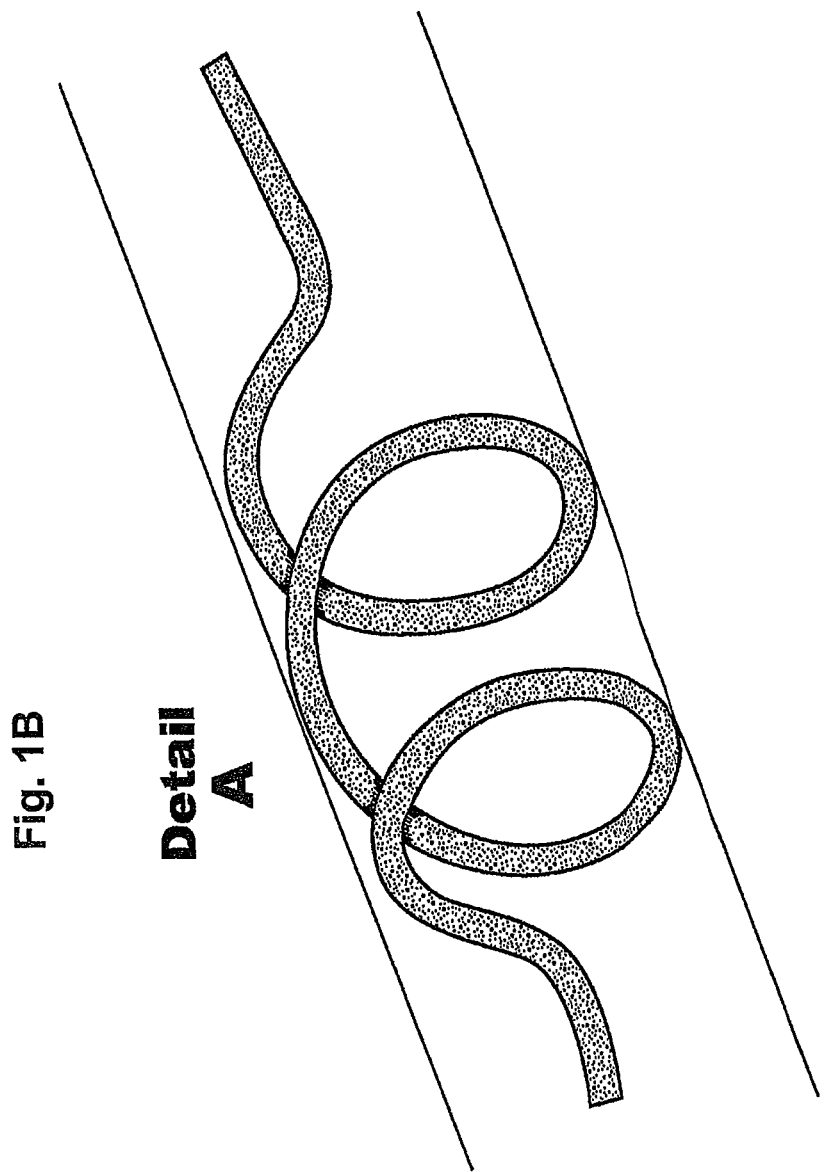
FIG. 1B is an exploded sectional view take from FIG. 1A.

The intravenous access port shown in FIG. 1 comprises a casing 1, having a cavity 2, at the exterior end of an intravenous catheter 3. The catheter is introduced into a vein by a guide needle 4 (shown here partially retracted) that is a catheter insertion guide, and which is subsequently removed by complete retraction through a septum 5 while the catheter remains in place. The guide needle is configured such (e.g. by using a notched needle) that visual confirmation of successful vessel entry is accomplished. A handle 6 of the port facilitating introduction into the vein consists of two elements (shown in the disassembled state during retraction of the guide needle 4) and is configured such that following removal of the guide needle its sharp bevel gets protected for increased safety. The cavity 2 has a further septum 7 for the entrance of a connecting cannula. The casing 1 of the port has a rim 8 which serves for attachment to a coupling element for connection between the port and an injection or blood sampling unit. The coupling element will be described in the following with reference to FIG. 2.

In an alternative embodiment preferentially applied in the case that the intravenous catheter is introduced into the vein at a place of the body, e.g. the crook of the arm, which is not suited for placement of the device directly above the catheter insertion site a handle with a stabilization platform of soft and flexible material is attached to the catheter between its tip and the port (not shown). This facilitates correct placement of the catheter and of the port and helps to minimize catheter movement in the vessel.

In Detail A the indwelling tip of the intravenous catheter is shown in a preferred configuration to avoid the direct contact of injection fluid with the vessel wall, which could cause local irritation. The catheter is pre-formed to take the shape of a spiral with the orifice geared to become centered and the circumference of the spiral prevents the contact between orifice and vessel wall and injection fluid delivered through the orifice gets immediately diluted by the flowing blood before getting into contact with the vessel wall. For introduction into the vein the spiral is stretched by the guide needle or wire and upon its retraction the catheter returns to its pre-imprinted spiral form shown.

The coupling element which is shown in FIG. 2a as a diagrammatic top view has a base plate 9 of a preferentially longitudinal shape for attachment to the arm of a patient and can be slightly concave to fit the shape of the body surface better. It has an opening 10 for positioning and adapting the port. For the preferred embodiment described in FIG. 1 for the case that the intravenous catheter is introduced into the vein e.g. at the crook of the arm and has a separate handle between the tip of the catheter and the port for catheter introduction, this opening can pass over to a slit (not shown) which opens one side of the base plate to accommodate and protect the part of the intravenous catheter which is lying on the skin between the handle and the port.

In the embodiment shown, the means for positioning and fixing the port is a U-shaped bolt 11 sliding in a slot of the coupling element and engaging firmly with a keyway of the port upon pushing, facilitated by a handle 12 of the bolt. The means for positioning an injection unit depicted in the example shown is a rim 13 on the upper surface of the coupling unit, having a keyway 14 for fixing a spring mechanism of the injection unit. The coupling element is attached to the skin by an adhesive layer 15.

FIG. 2b shows a sectional view of the coupling element along the axis indicated in FIG. 2a by the dot-and-dash line. It shows the means 16 for positioning the port in the opening of the coupling element and depicts in cross section the U-shaped bolt 11 with the handle 12 for fixing the port to the side wall 16 of the opening 10, as well as the rim 13 for positioning the injection unit.

Figure 3:
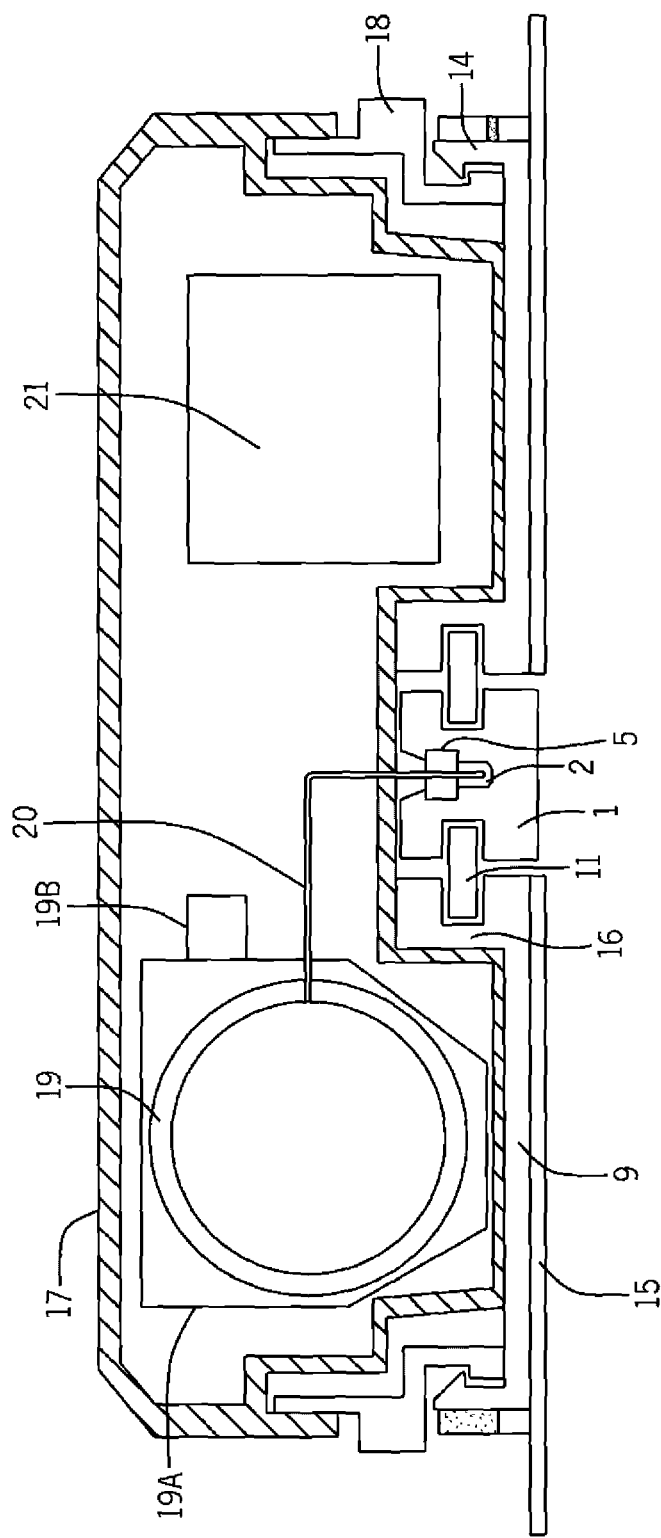
FIG. 3 is a diagrammatic cross sectional view of a device for intravenous delivery of injection fluid into a patient with port, coupling element and injection unit assembled.

The means for positioning and fixing the port and the injection or blood sampling unit relative to each other are further exemplified in FIG. 3 in a cross-sectional diagram. The coupling unit is attached directly to the skin by an adhesive layer 15, and since the port and the injection or blood sampling unit are firmly attached to the coupling unit this adhesive layer forms the adhesive contact surface for temporary wearing of the entire device on the skin.

FIG. 3 is a diagrammatic cross sectional view of a device for intravenous delivery of injection fluid into a patient with port, coupling element and injection unit assembled.

This figure shows the casing of the port 1 being fixed to the coupling element by bolt 11 engaging firmly in a keyway in the side wall 16 of the coupling element's opening 10. The base plate of the coupling element 9 is attached to the skin by the adhesive layer 15.

The injection unit has a housing 17 being fixed to the coupling element by a hook mechanism 18 formed in this embodiment as a spring mechanism engaging with a fixture 14 in the form of a keyway on the coupling element. This spring mechanism allows automatic coupling upon mounting the injection unit on the coupling element and manual decoupling by simultaneously pressing on the mechanism on both sides of the injection unit.

In the embodiment shown, the injection unit has a syringe pump 19A, generically referred to as a pump, preferentially a syringe pump the barrel of which is curved in the shape of a segment of a toroidal tube 19, but other kinds of pumps, as known in the prior art, can be employed and the use of a mechanical drive 19B (e.g. a clockwork drive) moved by an electric motor or other drives known in the prior art and many combinations of electronic, mechanical, pneumatic and hydraulic elements for delivery and control are possible. For constant delivery of injection fluid, the drive mechanism can be simplified to e.g. a spring as the displacement element.

Injection fluid can be delivered either continuously, or in accordance with the amount required, for example with respect to the concentration of the active substance delivered or of a related analyte, e.g. of glucose for the delivery of insulin. To this end, a blood sampling unit with a second cannula can be connected to e.g. a mini-sensor for glucose, which is also connected to the port via a second septum and a second cavity, and the cavities for injection fluid delivery and blood sampling are preferentially linked to a dual lumen intravenous catheter, with the orifice of the injection fluid delivery lumen being downstream in the vein to the orifice of the blood sampling lumen. Alternatively, a blood sampling unit with measuring means for one or several analytes or other devices measuring analytes or vital functions, e.g. heart or brain signals at other places, remote from the injection fluid delivery device, can provide the signals for the controlled delivery of injection fluid by wireless transmission.

Alternatively, such a syringe pump can be also used for very precise removal of blood and also for this use a construction with a syringe pump the barrel of which is curved in the shape of a segment of a toroidal tube has the great advantage of a compact footprint well suited for direct attachment to the skin.

FIG. 4 shows a diagrammatic view of an alternative embodiment of a device for intravenous delivery of injection fluid into a patient with port, coupling element and injection unit assembled. In such an alternative preferred embodiment the pump of the injection unit has a flexible reservoir with a rigidly connected cannula, and the flexible fluid reservoir is squeezed by a pressurized receptacle connected to a gas generating cell with a controller or control unit implemented as an electrical circuit, controlling the amount of gas produced via regulating the current drawn from the gas generating cell. The flexible reservoir can be manufactured preferentially by conventional blow-fill-seal technology. Such a pump results in a very compact design, and is therefore well suited for direct attachment to the skin even at higher injection fluid volumes up to 20 ml.

Whereas in the embodiment shown in FIG. 3 the assembly between the housing of the injection unit and the coupling element and concurrent piercing of the septum of the port by the cannula is achieved by a vertical movement, in the embodiment of the device shown in FIG. 4 the assembly and coupling between the housing of the injection unit and the coupling element and concurrent piercing of the septum of the port by the cannula is accomplished by a horizontal sliding movement.

Figure 4A:
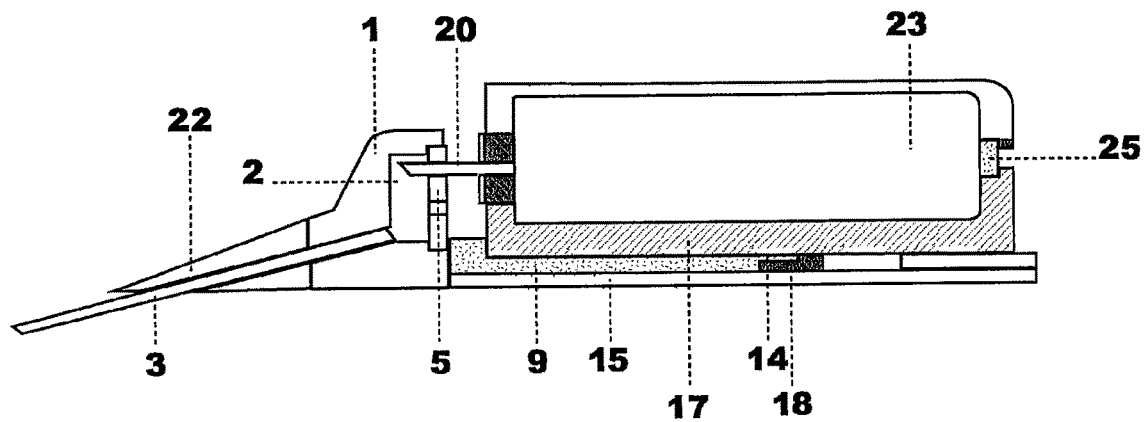
FIG. 4a is a diagrammatic cross sectional view and FIG. 4b is a horizontal sectional view of an alternative embodiment of a device for intravenous delivery of injection fluid into a patient with port, coupling element and injection unit assembled.

FIG. 4a shows a cross sectional view of the device with port, coupling element and injection unit assembled. The casing of the port 1 is fixed to the coupling element by a bolt mechanism (not shown). The base plate of the coupling element 9 is attached to the skin by the adhesive layer 15. The housing 17 of the injection unit is fixed to the coupling element with a hook mechanism 18 sliding under a fixture 14 on the coupling element in form of a depression. The base plate of the coupling element 9 may have a tunnel-shaped appendix 22 of flexible, semi-soft material as protection of the intravenous catheter in case the device can not be placed directly above the intravenous puncture site, e.g. if a vein in the crook of the arm is used for the venipuncture.

Figure 4B:
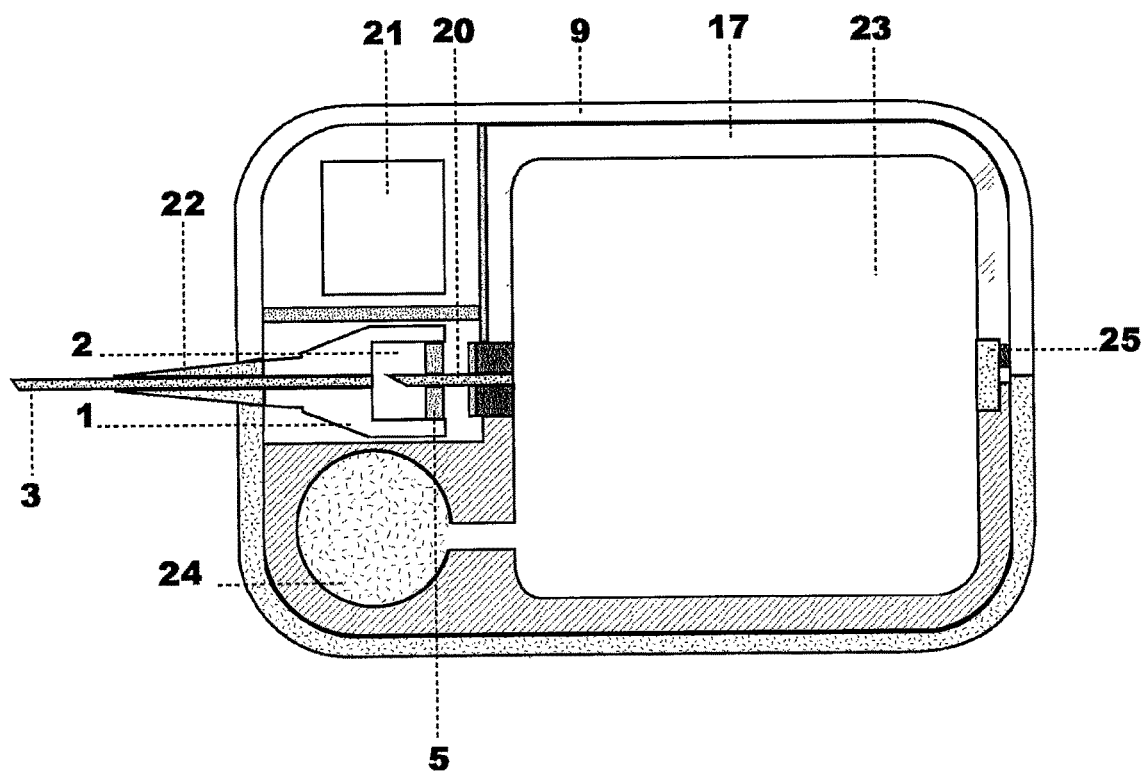

FIG. 4b shows a horizontal sectional view of the device. In the embodiment shown, the injection unit comprises a pump with a flexible fluid reservoir 23 and a gas-tight housing 17 as pressurized receptacle, but other embodiments e.g. with a separate displacement bag as pressurized receptacle are also possible. The pressurized receptacle is exerting pressure against the fluid reservoir causing a positive displacement of injection fluid by compressing this collapsible reservoir. The pressurized receptacle is connected to a gas generating cell 24. The contents of the flexible reservoir 23 are discharged through the cannula 20, through the septum 5, into the cavity 2 of the port which opens towards the intravenous catheter 3 delivering the injection fluid into the patient's vein. In the embodiment shown, control of the amount of gas produced by the gas generating cell is regulated electronically by a control unit 21, preferentially by regulating the current drawn from the gas generating cell. The flexible fluid reservoir 23 can be manufactured already filled with injection fluid or be an evacuated bag with a septum 25 allowing filling with e.g. a syringe.

A great advantage of the construction according to the present invention compared to similar known devices is that the device is attached to the skin and avoids the problems with connecting tubes between an infusion pump and the intravenous catheter.

The replacement of connecting tubes by direct connection between the intravenous catheter and the device and simplification of assembly and operation results in improved safety and is important for acceptance by patients and non-specialized health care professionals.

In addition, the dead volume between pump and the tip of the intravenous catheter is by the use of connecting tubes in known devices significant necessitating the withdrawal of blood to move the air out of the system before infusion can be started. Further, sampling of blood for analysis inevitably leads to blood leakage which should be avoided for safety reasons and the dead volume of the connecting tube necessitates withdrawal of unnecessary large volumes of blood. The subject invention allows including all safety features of modern intravenous catheter systems while also solving the above mentioned problems with a compact device of simple construction as depicted in FIGS. 3 and 4.

Of course the pump for delivery of injection fluid into a patient, or for removal of blood from a patient and their drive means or the coupling mechanisms between port, coupling element and injection or blood sampling unit could be achieved via numerous alternative possibilities, as known in the prior art. Moreover, the coupling element is fused with the port. Further, a large variety of diagnostic elements for the online analysis or for sampling of removed blood as well as control and measuring means and control functions for delivery of injection fluid can be accommodated with the device and it will be apparent to one of ordinary skill in the art that many variations, modifications and adaptations to special applications and needs can be made while remaining within the spirit and scope of the invention.

A device, according to an embodiment of the invention, for intravenous delivery of injection fluid into a patient, or for removal of blood from a patient which is adhering to the skin and including a port at the exterior end of an intravenous catheter having a cavity with at least one septum, an injection or blood sampling unit, a coupling element having means for positioning and fixing the port and the injection or blood sampling unit relative to each other and having an adhesive contact surface for securing onto the patient. The port has a cavity with two or more integrated septums, one as an entrance for a guide needle or wire for the introduction of the catheter into a vein, which can thereafter be removed through that septum and other septums as an entrance for connecting cannulas.

The invention claimed is:
1. A device for intravenous access, comprising:
a connection cannula;
a fluid delivery device or blood sampler including therein a controller and a pump, and being connected to the connection cannula;
an intravenous catheter to be placed into a vein of a patient;
a catheter insertion guide for guiding the intravenous catheter;
a port including a cavity therein, the cavity being for connection to an exterior end of the intravenous catheter, the port including an attachment portion, the cavity including a first septum configured to be pierced by the intravenous catheter, and a second septum configured to be pierced by the connection cannula for fluid connection from the fluid delivery device or blood sampler to the cavity; and a coupler for positioning and fixing the port, the coupler including a base plate with an adhesive contact surface to attach onto skin of the patient and a holder engaging with the attachment portion of the port to secure the port and the fluid delivery device or blood sampler with the coupler for fluid connection between the port and the fluid delivery device or blood sampler unit through the connection cannula.

2. The device according to claim 1 wherein the cavity includes a third septum.

3. The device according to claim 1 wherein the coupler is fused with the port.

4. The device according to claim 1, wherein the pump is for delivery or withdrawal of fluid and comprises a syringe pump.

5. The device according to claim 4 wherein a barrel of the syringe pump is curved in a shape of a segment of a toroidal tube with an axis of the tube including a segment of a circle.

6. The device according to claim 1, further comprising:
an injection unit,
wherein the injection unit and the blood sampler are both connected to the port.

7. The device according to claim 6, wherein the blood sampler further comprises a measuring system for one or several analytes.

8. The device according to claim 6, wherein the blood sampler including a receptacle to collect blood samples that avoids mixing the samples over time.

9. The device according to claim 6, wherein the blood sampler introduces segments of air or a non-miscible fluid to avoid mixing samples over time.

10. The device according to claim 1, wherein the pump is for delivery of fluid and includes a flexible reservoir and a driver causing a positive displacement of injection fluid by compressing the flexible reservoir and a controller to regulate the fluid delivery.

11. The device according to claim 10 wherein the driver causing a positive displacement of injection fluid by compressing the reservoir is pressurized gas produced by a gas generating cell and the controller to regulate flow is an electrical circuit regulating current drawn from the gas generating cell.

12. The device according to claim 1 wherein an intravenous end of the catheter is pre-formed in the shape of a spiral with an orifice geared to become centered in order to avoid direct contact of the orifice with an intravenous wall, and is stretched for introduction into a vein of the patient with a guide needle or wire.

13. A method for intravenous access, comprising:
placing an intravenous catheter with a port of a device into a vein of a patient, the port including a casing with a cavity therein, the cavity being for connection to an exterior end of the intravenous catheter, the casing having an integral attachment portion, the cavity including a first septum configured to be pierced by the intravenous catheter, and a second septum configured to be pierced by a connection cannula for fluid connection from a fluid delivery device or blood sampler to the cavity, the fluid delivery device or blood sampler including therein a controller and a pump; and
positioning over and fixing to the port a coupler, the coupler for positioning and fixing the port, the coupler including a base plate with an adhesive contact surface to attach onto skin of the patient and a holder engaging with the attachment portion of the port to secure the port and the fluid delivery device or the blood sampler in the coupler for fluid connection between the port and the fluid delivery device or blood sampler unit through the connection cannula.

14. The method according to claim 13, further comprising:
attaching to the coupler an injection or blood sampler with the connection cannula piercing the second septum of the port; and
starting an injection and/or blood sampling process through the vein, through the catheter, through the port, and through the connection cannula.

15. The method according to claim 14, wherein:
the starting performs the injection which includes an ambulant injection of medicine.

16. The method according to claim 14, wherein:
the starting performs the blood sampling process which performs an ambulant measuring of concentration-time profiles of analytes in blood.

17. The method according to claim 16, wherein:
the starting further performs the injection in order to perform ambulant profiling of a metabolic and drug metabolizing status of subjects by administering, using the injection, one or several substances or drugs to an individual and measuring, using the blood sampling process, the resulting concentration-time profiles, including metabolites.

* * * * *